US012629182B2

(12) United States Patent
Kearns

(10) Patent No.: US 12,629,182 B2
(45) Date of Patent: May 19, 2026

(54) ARTHRODESIS DEVICE

(71) Applicant: IN2BONES, Ecully (FR)

(72) Inventor: Stephen Kearns, Barna (IE)

(73) Assignee: In2Bones, Ecully (FR)

( * ) Notice: Subject to any disclaimer, the term of this patent is extended or adjusted under 35 U.S.C. 154(b) by 49 days.

(21) Appl. No.: 16/967,816

(22) PCT Filed: Feb. 6, 2019

(86) PCT No.: PCT/FR2019/050263
§ 371 (c)(1),
(2) Date: Aug. 6, 2020

(87) PCT Pub. No.: WO2019/155160
PCT Pub. Date: Aug. 15, 2019

(65) Prior Publication Data
US 2021/0038269 A1 Feb. 11, 2021

(30) Foreign Application Priority Data
Feb. 7, 2018 (FR) ...................................... 1851024

(51) Int. Cl.
*A61B 17/72* (2006.01)
*A61B 17/17* (2006.01)
(Continued)

(52) U.S. Cl.
CPC ...... *A61B 17/7291* (2013.01); *A61B 17/1717* (2013.01); *A61B 17/1725* (2013.01);
(Continued)

(58) Field of Classification Search
CPC ............ A61B 17/7291; A61B 17/1725; A61B 17/1775; A61B 17/1717; A61B 17/72;
(Continued)

(56) References Cited

U.S. PATENT DOCUMENTS

| | | | | |
|---|---|---|---|---|
| 5,034,013 A | * | 7/1991 | Kyle | .................. A61B 17/7266 606/62 |
| 5,035,697 A | * | 7/1991 | Frigg | ................. A61B 17/7283 606/86 R |

(Continued)

FOREIGN PATENT DOCUMENTS

| | | |
|---|---|---|
| WO | 2006/091460 A1 | 8/2006 |
| WO | 2011/072249 A1 | 6/2011 |

*Primary Examiner* — Marcela I. Shirsat
(74) *Attorney, Agent, or Firm* — Rutan & Tucker LLP; Hani Z. Sayed

(57) ABSTRACT

The invention relates to an ankle arthrodesis device comprising a pin (1) intended to be implanted in a tibia (Ti), a talus (Ta) and a calcaneus (Ca), the pin (1) comprising a proximal portion (2) extending along a first direction (A-A'), and a distal portion (4) extending along a second direction (B-B') that intersects the first direction (A-A'), the distal portion (4) being provided with a first oblong attachment opening along the second direction (B-B'), the device comprising a first compressive attachment means (9A), of the compression screw type (9A), the pin (1) being designed and configured such that, when it is implanted with its distal portion (4) oriented toward the back of the ankle, the first attachment opening is arranged to receive and guide the first attachment means (9A) along a first attachment direction (F1-F1') extending along said talus (Ta) and calcaneus (Ca) to attach the nail to the talus (Ta) and to the calcaneus (Ca).

8 Claims, 3 Drawing Sheets

(51) Int. Cl.

| | |
|---|---|
| *A61B 17/56* | (2006.01) |
| *A61B 17/68* | (2006.01) |
| *A61B 17/74* | (2006.01) |
| *A61B 17/84* | (2006.01) |

(52) U.S. Cl.
CPC ..... *A61B 17/1775* (2016.11); *A61B 2017/564* (2013.01); *A61B 2017/681* (2013.01); *A61B 17/7225* (2013.01); *A61B 17/7233* (2013.01); *A61B 17/7241* (2013.01); *A61B 17/725* (2013.01); *A61B 17/7283* (2013.01); *A61B 17/744* (2013.01); *A61B 17/846* (2013.01)

(58) Field of Classification Search
CPC ........... A61B 17/7233; A61B 17/7241; A61B 17/725; A61B 17/7283; A61B 17/744; A61B 17/846; A61B 2017/564; A61B 2017/681
USPC ......................................... 606/329, 86 R, 62
See application file for complete search history.

(56) References Cited

U.S. PATENT DOCUMENTS

| | | | | |
|---|---|---|---|---|
| 2003/0069581 | A1* | 4/2003 | Stinson .................. | A61B 17/72 606/62 |
| 2005/0055024 | A1* | 3/2005 | James ................ | A61B 17/1668 606/64 |
| 2006/0064096 | A1* | 3/2006 | Prien .................... | A61B 17/725 606/64 |
| 2006/0200141 | A1* | 9/2006 | Janna ................. | A61B 17/7291 606/62 |
| 2011/0282397 | A1* | 11/2011 | Richter ............. | A61B 17/1725 606/301 |
| 2012/0109217 | A1* | 5/2012 | Perineau ........... | A61B 17/7291 606/301 |
| 2012/0130370 | A1 | 5/2012 | Kinmon | |

* cited by examiner

ARTHRODESIS DEVICE

This is a National Phase Application filed under 35 U.S.C. 371 as a national stage of PCT/FR2019/050263, filed Feb. 6, 2019, an application claiming the benefit of French Application No. 1851024, filed Feb. 7, 2018, the content of each of which is hereby incorporated by reference in its entirety.

TECHNICAL FIELD

The present invention relates to the general technical field of devices intended to be used to carry out an arthrodesis and, more specifically, to carry out an arthrodesis of the joint of an ankle, in particular in the context of an orthopedic treatment.

More specifically, the invention concerns an ankle arthrodesis device comprising a nail intended to be implanted in a tibia, a talus and a calcaneus of a patient, said nail comprising a proximal portion which generally extends according to a first longitudinal direction of extension, and a distal portion which prolongs said proximal portion and generally extends according to a second longitudinal direction of extension, said distal portion being provided with a first fastening orifice.

PRIOR ART

In order to treat some bone pathologies of the ankle, such as an osteoarthritis, resulting in a deterioration or a disappearance of the articular cartilage, it is known to proceed with an arthrodesis of the joint of the concerned ankle, that is to say a surgical intervention intended to suppress all or part of the mobility of the joint of the ankle by causing an osteosynthesis (or «bone fusion») of the involved bone bodies.

In order to carry out such interventions, it is known to use an arthrodesis device comprising an arthrodesis nail, intended to be implanted at the level of the joint of the ankle. This nail is generally introduced into rooms successively formed through the different bone bodies forming the concerned joint, and then fastened to the latter, so as to immobilize the joint of the ankle and to promote a bone fusion of these bone bodies. In general, the implementation of such an arthrodesis nail comprises, after implantation of the nail and before fastening of the latter, an operation of compressing the bone bodies of the joint of the ankle, intended to bring these bone bodies, and in particular the calcaneus and the tibia, close to one another in particular in order to promote a proper bone fusion of the latter.

While such known arthrodesis devices are generally satisfactory and have, to date, allowed for a substantial improvement in the treatment of patients suffering from advanced bone pathologies of the ankle, they are still to be perfected. Indeed, it has been in particular observed that, once implanted in the body of the patient, the arthrodesis nail of such devices may in some cases lack stability in use and lead to an insufficient holding of the bone bodies of the concerned joint. This results in a risk of a faulty osteosynthesis of the bone bodies of the ankle.

DISCLOSURE OF THE INVENTION

Consequently, the objects assigned to the present invention aim at addressing the aforementioned drawbacks and at providing a new arthrodesis device comprising a nail which, once implanted in the joint of the ankle of a patient, has, by its configuration, an excellent stability while allowing for an improved holding of the bone bodies of the ankle in order to promote the bone fusion of the latter.

Another object of the invention aims at providing a new arthrodesis device comprising an arthrodesis nail particularly suited to the anatomy of the joint of the ankle.

Another object of the invention aims at providing a new arthrodesis device comprising a nail which may be fastened in a particularly effective way in the bone bodies of the joint of the ankle.

Another object of the invention aims at providing a new arthrodesis device comprising an arthrodesis nail with a design that is simple and inexpensive to manufacture.

Another object of the invention aims at providing a new arthrodesis device allowing performing an effective compression of the joint of the ankle.

Another object of the invention aims at providing a new arthrodesis device allowing treating a bone pathology of the ankle of the patient in a particularly effective and rapid way.

The objects assigned to the invention are achieved by means of an ankle arthrodesis device comprising a nail intended to be implanted in a tibia, a talus and a calcaneus of a patient, said nail comprising:

a proximal portion which generally extends according to a first longitudinal direction of extension, and a distal portion which prolongs said proximal portion and generally extends according to a second longitudinal direction of extension secant to said first longitudinal direction of extension, said distal portion being provided with a first fastening orifice which is oblong according to said second longitudinal direction of extension, said device comprising a first compressive fastening means, such as a compressive screw, said nail being designed and configured so that, when said nail is implanted with said distal portion directed rearwards of the ankle of the patient, said first fastening orifice is arranged so as to receive and guide said first fastening means according to a first fastening direction which extends through said talus and calcaneus so as to fasten said nail to said talus and to said calcaneus.

BRIEF DESCRIPTION OF THE DRAWINGS

Other particularities and advantages of the invention will appear and come out in more detail on reading the description provided hereinafter, made with reference to the appended drawings, provided only as an illustrative and non-limiting example, in which.

BEST WAY TO CARRY OUT THE INVENTION

The invention concerns an arthrodesis device, designed so as to be implemented in the context of an arthrodesis of the joint of an ankle of a patient, in particular when the latter is in a state of deterioration that is too advanced for other less severe surgical interventions being technically adapted. Preferably, the patient concerned by the arthrodesis device is a human patient. More specifically and advantageously, the ankle arthrodesis device according to the invention is a device for tibiotalocalcaneal (TTC) arthrodesis by nailing, preferably transplantar, and still preferably through a backward approach. As example, the arthrodesis device according to the invention can advantageously be implemented to treat a patient suffering from an advanced form of degenerative osteoarthritis, post-traumatic osteoarthritis, inflammatory osteoarthritis, necrosis of the talus, Charcot osteoarthropathy, and even in the event of failure of one or several surgeries, such as a total joint replacement (replacement of the joint of the ankle by a total ankle prosthesis (TAP)).

The arthrodesis device according to the invention comprises an arthrodesis nail 1 intended to be implanted, preferably through a plantar approach, in a tibia Ti, a talus Ta and a calcaneus Ca of a patient, in general during a surgery carried out under general or loco-regional anesthesia. Advantageously, the joint of the considered ankle would have undergone, prior to the set-up of the nail 1 in the body of the patient, an adequate preparation, and for example bone sections and an extraction of cartilaginous elements between the tibia Ti and the talus Ta (tibiotalar joint) on the one hand and between the talus Ta and the calcaneus Ca (talocalcaneal joint) on the other hand, so as to suppress all or part of the natural joint surfaces of the joint of the ankle to be treated, in order to promote the bone fusion. Also, a room would have advantageously been formed beforehand within said tibia Ti, talus Ta and calcaneus Ca, using any known means, in order to receive said nail 1.

It should be noted herein that, in some cases, the joint of the ankle to be treated using the arthrodesis device according to the invention may be deprived of a talus as such, in particular following a surgical ablation of the latter, too deteriorated to be preserved as it is. In this respect, the term «talus» used in the present description advantageously refers to the talus Ta as a natural bone body (physiological talus), but may, where appropriate, refer to the empty joint space corresponding to the talus when the latter is absent, or else to a substitute talar implant (or any equivalent element aiming at filling the joint space formed by the absence of talus).

Figures 1, 2, 3:
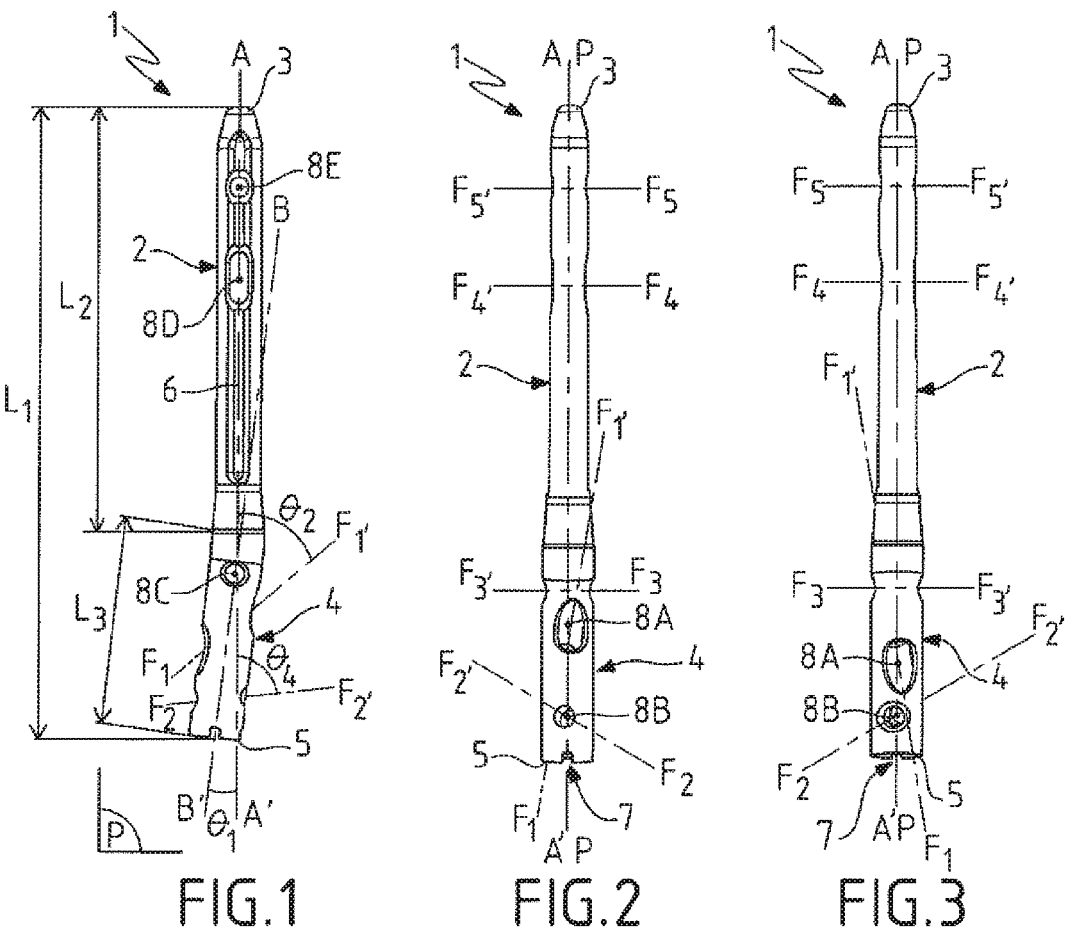
FIG. 1 illustrates, according to a side view, a preferred embodiment of the nail of an arthrodesis device in accordance with the invention, which nail comprises a proximal portion which generally extends according to a first longitudinal direction of extension and a distal portion which prolongs said proximal portion and generally extends according to a second longitudinal direction of extension, which is secant to said first direction of extension.
FIGS. 2 and 3 respectively illustrate according to anterior (FIG. 2) and posterior (FIG. 3) views, the nail of FIG. 1.

A preferred embodiment of the nail 1 of the device according to the invention is illustrated in FIGS. 1 to 3. The nail 1 illustrated as example in these figures is intended to be set in place at the level of the joint of a right ankle of a patient. Of course, the invention also covers an arthrodesis device comprising a nail that would be intended to be set in place at the level of the joint of a left ankle of a patient Advantageously, such a nail for a left ankle would be defined by symmetry of the nail 1 illustrated in the figures, with respect to the sagittal plane of the patient.

Said nail 1 comprises, on the one hand, a proximal portion 2, which generally extends according to a first longitudinal direction of extension A-A', preferably from a free proximal end 3 of the nail 1. On the other hand, the nail 1 comprises a distal portion 4, which advantageously prolongs said proximal portion 2, and generally extends according to a second longitudinal direction of extension B-B', preferably up to a free distal end 5 of the nail 1, opposite to said proximal end 3.

According to the preferred embodiment illustrated in the figures, both said proximal portion 2 and distal portion 4 are elongate and preferably substantially rectilinear, respectively according to said first A-A' and second B-B' directions of extension. As illustrated in FIGS. 1 to 3, the nail 1 preferably has the general shape of a rod, preferably solid.

Preferably, the proximal portion 2, still preferably as well as the distal portion 3 of the nail 1, has a cylindrical general shape (with a circular section). Alternatively, the proximal portion 2 and the distal portion 3 could have a conical general shape (with a circular section), or one amongst the proximal portion 2 and distal portion 3 could have a conical general shape whereas the other one has a cylindrical general shape. Such a cylindrical and/or conical general shape advantageously facilitates the set-up of the nail 1 through the concerned bone bodies and tissues.

Preferably, the proximal portion 2 of the nail 1 is provided with a means for blocking the rotation of the nail 1 about said first direction of extension A-A'. Preferably, said blocking means comprises at least one longitudinal groove 6 or fin. However, said blocking means may alternatively comprise at least one longitudinal flattened surface or any other suitable means. In the example illustrated in the figures, the proximal portion 2 of the nail 1 comprises two longitudinal grooves 6, positioned symmetrically with respect to the first direction of extension A-A' of said proximal portion 2.

Advantageously, such longitudinal grooves 6 may further allow reducing the forces exerted by the nail 1 within the tibia Ti, by locally reducing the bulk volume of the nail 1.

Of course, the nail 1 may possibly have a general shape different from that disclosed hereinabove, for example that shape of a rod with an oval or polyhedral section. Also, said proximal 2 and distal 4 portions may have sections with different sections from one another.

Preferably, the nail 1 is monolithic and therefore forms an integral part, made in one-piece. Advantageously, said nail 1 is made of a biocompatible material (by nature or made biocompatible following a treatment) and adapted to withstand the characteristic biomechanical stresses of an ankle, such as for example stainless steel, a titanium alloy, a chromium-cobalt alloy, or else a polymer material, such as for example polyether-ether-ketone (PEEK), whether charged or not.

Figure 5:
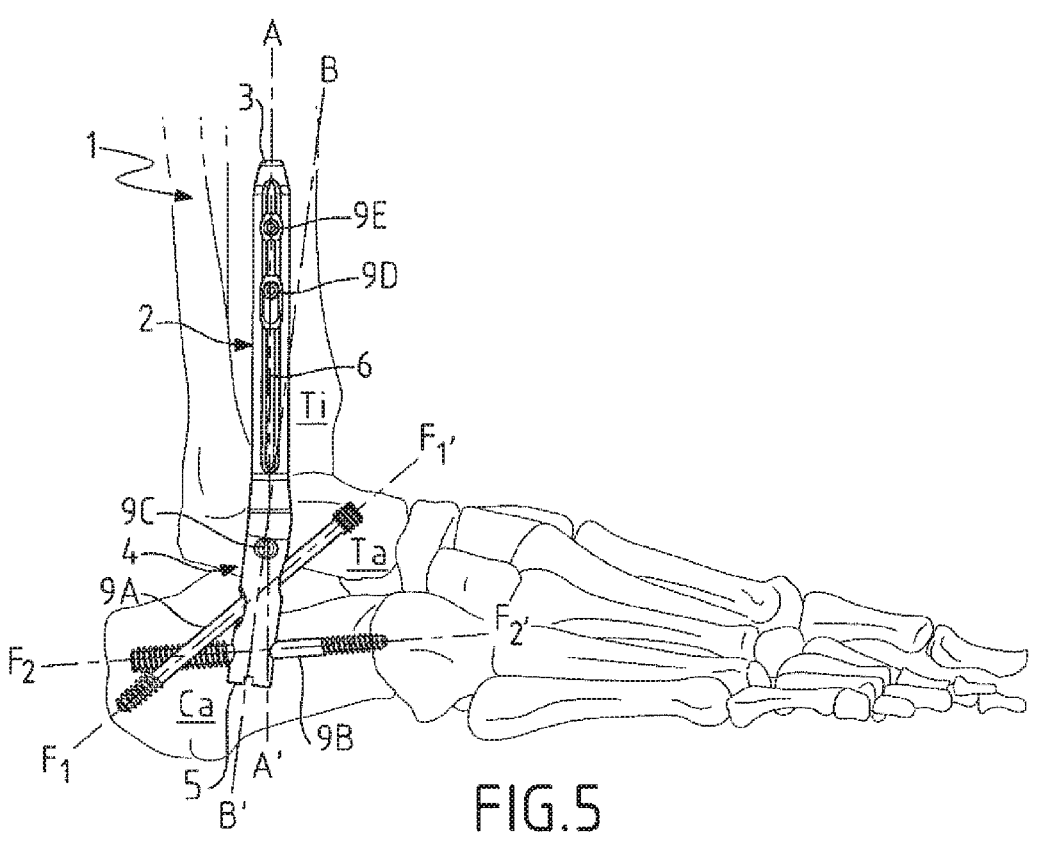
FIGS. 5 and 6 respectively illustrate according to a side view (FIG. 5) and according to a perspective middle view (FIG. 6), the nail of the previous figures, implanted in a joint of a right ankle of a patient. In these figures, the considered nail is fastened to the bone bodies of the joint of the ankle using a plurality of fastening means independent from the nail.

Preferably, the proximal portion 2 of the nail 1 is intended to be mostly inserted and positioned into the tibia Ti of the patient, preferably within the medullary canal of the latter (intramedullary nail), such that the first direction of extension A-A' of said proximal portion 2 of the nail 1 is substantially parallel to (when not coincident with) the axis of vertical extension of the tibia Ti. In turn, the distal portion 4 of the nail is preferably intended to be mostly inserted and positioned into the corresponding calcaneus Ca of the patient (FIG. 5). As illustrated in the figures, both of said proximal 2 and distal 4 portions may advantageously be inserted and positioned partially, in a minor amount, into the talus Ta.

Advantageously, the proximal end 3 of the nail 1 may be rounded or chamfered in order to facilitate the insertion and guidance of the nail 1 within the concerned calcaneus C, talus T and tibia Ti.

According to the invention, the respective first A-A' and second B-B' directions of the proximal 2 and distal 4 portions of the nail 1 are secant to one another, that is to say the nail 1 is curved, as could be observed in FIGS. 1 to 3 in particular. Thus, the free proximal 3 and distal 5 ends of the nail 1 advantageously have a shift therebetween. Advantageously, when the nail 1 of the arthrodesis device according to the invention is implanted so that the first direction of extension A-A' of the proximal portion 2 of the nail 1 is substantially parallel to (when not coincident with) the axis of vertical extension of the tibia Ti, the distal portion 4 of the nail 1 may then extend through the calcaneus Q in an oblique manner with respect to the axis of vertical extension of the tibia Ti (FIG. 5). Such an angle allows advantageously increasing the length of travel of the distal portion 4 of the nail 1 within the calcaneus Ca, which confers an improved stability on said nail 1, at least at the level of the concerned calcaneus Ca.

Advantageously, the respective first A-A' and second B-B' directions of extension of the proximal 2 and distal 4 portions are secant according to a first angle 81 comprised between 5 and 10°±2°, and preferably equal to 7°±2°. Indeed, such an angular value provides a very good tradeoff in terms of mechanical stability conferred on the nail 1 by the angle, yet without excessively altering the ease of set-up of said nail 1 within the joint of the patient ankle.

In the preferred embodiment illustrated in the figures, the nail 1 is designed and dimensioned so that, when said nail 1 is implanted in the joint of the ankle, the point of intersection of the respective first A-A' and second B-B' directions of extension of the proximal 2 and distal 4 portions of the nail 1, located nearby at the level of the junction of the latter, is positioned within the corresponding talus a of the patient (FIGS. 5 to 8).

In order to enable fastening and holding of the nail 1 in position within the joint of the ankle, once said nail 1 is inserted into said tibia Ti, talus Ta and calcaneus Ca, the distal portion 4 of the nail 1 is provided with at least one first fastening orifice 8A. The latter crosses the nail 1 therethroughout, and is intended to receive and guide a first fastening means 9A of the nail 1 within the joint of the ankle. While not necessarily comprised in the arthrodesis device according to the invention, said first fastening means 9A may for example consist of a screw, as will be seen later on.

According to the invention, the nail 1 is more specifically and advantageously designed and configured so that, when said nail 1 is implanted with said distal portion 4 directed rearwards of the ankle of the patient (FIGS. 5 and 6), said first fastening orifice 8A is arranged, and in particular directed, so as to receive and guide said first fastening means 9A according to a first fastening direction $F_1$-$F_1$' which extends through said talus Ta and calcaneus C, so as to fasten said nail 1 to the considered talus Ta and calcaneus S. Preferably, the main axis of extension of the first fastening orifice 8A through the nail 1 is coincident with said first fastening direction $F_1$-$F_1$'. As shown in the figures, said first fastening orifice 8A opens onto a front face and an opposite rear face of the distal portion 4 of the nail 1 (considering the front and the rear of the ankle when the nail 1 is implanted), and advantageously extends in an oblique manner with respect to the second direction B-B' of the distal portion 4 of the nail 1.

Thus, it forms through the nail 1 a conduit whose main axis of extension through the nail 1 is oblique with respect to said second direction B-B'. 1s Thanks to this particular configuration of the nail 1, the first fastening means 9A, properly dimensioned, is advantageously adapted to constitute a transarticular fastening means of the nail 1, which allows fastening the nail 1 in the joint of the ankle, by cooperation of said first fastening orifice 8A and first fastening means 9A, by immobilizing the talocalcaneal joint (or subtalar joint).

Thus, the underlying idea of the invention is an ankle arthrodesis device which comprises a nail 1 having both an angled shape which enables its distal portion to extend into the calcaneus C rearwards of the angle so as to ensure stability of the nail 1 in the calcaneus a, and a first fastening orifice 8A designed so as to receive and guide a first transarticular fastening means 9A so that the latter could cross the nail 1 therethroughout in order to ensure securing of the calcaneus Ca to the talus Ta (immobilization of the subtalar joint). This ingenious and original combination of features confers on the nail 1 of the arthrodesis device according to the invention an excellent mechanical stability in use and allows for a holding of the bone bodies of the joint of the ankle which is particularly advantageous for the achievement of a proper bone fusion.

Preferably, said first fastening orifice 8A is oblong according to said second direction of extension B-B' of the distal portion 4 of the nail 1. Thus, the distal portion 4 of the nail 1 keeps some degree of freedom in translation relative to the first fastening means 9A, according to said second direction of extension B-B', when the fastening means 9A is received and guided within the first fastening orifice 8A. Advantageously, the large diameter (measured according to the second direction of extension B-B') of said first fastening orifice 8A is comprised between 5 and 15 mm±1 mm, preferably equal to 13 mm±1 mm.

Preferably, besides the nail 1, the arthrodesis device comprises said first fastening means 9A, which preferably consists of a screw, as commonly known and used in the field.

According to one variant (not illustrated), said first fastening means 9A consists of a non-compressive screw.

According to a particularly advantageous alternative variant, said first fastening means 9A, on the contrary, consists of an osteosynthesis compressive screw 9A. In other words, according to this variant, said first fastening means 9A is a compressive fastening means, that is to say a means designed so as to enable relative fastening of two bone bodies while ensuring a foreshortening and compression effect of these bone bodies during the set-up of the fastening means. In particular, such a first fastening means 9A may consist of an osteosynthesis compressive screw 9A, as in the preferred embodiment illustrated in the figures. Advantageously, such a compressive screw has at the level of its head a first tapping with a constant first pitch p1 and, at the level of its distal portion, a second tapping with a constant second pitch p2, the first pitch p1 being smaller than the second pitch p2. As illustrated, the compressive screw may comprise a non-tapped portion, which extends between the first and second tappings. Also sometimes called «compression bone screw», such a compressive screw 9A is known as such, and may possibly have a different design than that illustrated in the figures. Of course, such a compressive fastening means does not necessarily consist of a screw, and may be of any other suitable type.

The implementation of such a first compressive fastening means 9A in combination with the nail 1 disclosed hereinbefore allows for a better compression of the subtalar joint. Advantageously, said compressive screw 9A may be cannulated, in order to facilitate the set-up thereof, for example using a Kirschner wire. In the above-mentioned preferred case where the corresponding first fastening orifice 8A is oblong, said compressive screw 9A may advantageously be displaced, where needed, within the first fastening orifice 8A of the nail 1 during a subsequent operation of compressing the concerned bone bodies. Thus, the compression of the joint of the ankle may advantageously be carried out without loading the nail 1 itself.

Still alternatively, yet less advantageously, said first fastening means 9A may possible by of any suitable type, for example of the wire or nail type.

In order to best fit to the anatomy (and in particular to the length of the tibia Ti) of the patient, the nail 1 preferably has an overall length $L_1$, measured between its proximal 3 and distal 5 ends, comprised between 150 and 350 mm. Preferably, the proximal portion 2 of the nail 1 has a length $L_2$, measured according to said first direction of extension A-A', substantially comprised between 100 and 300 mm, whereas the distal portion 4 of the nail 1 has a length $L_3$, measured according to said second direction of extension B-B', substantially comprised between 45 and 55 mm. Preferably, the proximal 2 and distal 4 portions have a diameter comprised between 10 mm and 13 mm±1 mm. Still preferably, the distal portion 4 has a diameter larger than the respective diameter of the proximal portion 2.

As will be set out hereinafter, the nail 1 may advantageously comprise one or several other fastening orifice(s), each intended to receive and guide an additional fastening means, distinct from said first fastening means 9A disclosed hereinbefore, in order to participate to the proper anchorage of the nail 1 in the bone bodies of the joint of the concerned ankle.

Preferably, said distal portion 4 of the nail 1 is provided with a second fastening orifice 8B (or calcaneal fastening orifice), which is configured to receive and guide a second fastening means 9B according to a second fastening direction $F_2$-$F_2$' so as to fasten said nail 1 to the concerned calcaneus Ca of the patient. Advantageously, said second fastening orifice 8B is configured so as to receive and guide said second fastening means 9B in order to fasten the nail 1 only to said calcaneus Ca, that is to say so that said second fastening means 9B could cooperate with the corresponding talus Ta. In the example illustrated in the figures, said second fastening orifice 8B is positioned in the proximity of the free distal end 5 of the nail 1, between said first fastening orifice 8A and the free distal end 5 of the nail 1.

By advantageously enabling an implantation of the nail 1 with the distal portion 4 of the latter directed rearwards of the ankle of the patient, as mentioned hereinbefore, the curvature of the distal portion 4 of the nail with respect to the proximal portion 2 of the latter advantageously allows for a better longitudinal centering of the second fastening orifice 8B within the calcaneus Ca. In this manner, said second fastening orifice 8B is brought close to the posterior end of the calcaneus, in particular in the case of a nail that would be strictly rectilinear, which facilitates the set-up of said second fastening means 8B by the rear of the calcaneus (generally posterior approach). Besides, such a configuration advantageously allows forming a larger bone area available for the travel of the second fastening means 8B in the posterior portion of the calcaneus Cg. Anchorage of the distal portion 4 of the nail 1 to the calcaneus Ca is thus improved.

Preferably, said second fastening orifice 8B extends in an oblique manner with respect to the second direction B-B' of the distal portion 4 of the nail 1, that is to say it forms a conduit whose main axis of extension is oblique with respect to said second direction B-B'. Preferably, said second fastening orifice 8B is substantially cylindrical and the main axis of extension of the latter through the nail 1 is coincident with said second fastening direction $F_2$-$F_2$'.

Preferably, said distal portion 4 of the nail 1 is provided with a third fastening orifice 8C (or talar fastening orifice), which is configured so as to receive and guide a third fastening means 9C according to a third fastening direction $F_3$-$F_3$' in order to fasten said nail 1 to the concerned talus Ta of the patient. Preferably, the main axis of extension of said third fastening orifice 8C through the nail 1 is coincident with said third fastening direction $F_3$-$F_3$'. Preferably, said third fastening direction $F_3$-$F_3$' is orthogonal to the second direction of extension B-B' of the distal portion 4 of the nail 1. Advantageously, said third fastening orifice 8C is configured so as to receive and guide said third fastening means 9C in order to fasten the nail 1 only to said talus Ta, that is to say so that said third fastening means 9C could not cooperate with the corresponding calcaneus Ca.

In the preferred embodiment illustrated in the figures, said third fastening orifice 9C is arranged in the vicinity of the junction area between said proximal 2 and distal 4 portions of the nail 1 and of the point of intersection of the first A-A' and second B-B' 1s directions of extension, said first fastening orifice 8A being arranged between said third fastening orifice 8C and the free distal end 5 of the nail 1.

Preferably, the proximal portion 2 of the nail 1 is provided with a fourth fastening orifice 8D (first tibial fastening orifice), which is configured so as to receive and guide a fourth fastening orifice 9D according to a fourth fastening orifice $F_4$-$F_4$' in order to fasten said nail 1 to the concerned tibia Ti of the patient. Preferably, said fourth fastening direction $F_4$-$F_4$' is orthogonal to the first direction of extension A-A' of the proximal portion 2 of the nail 1. Advantageously, the main axis of extension of said fourth fastening orifice 8D through the nail 1 is coincident with said fourth fastening direction $F_4$-$F_4$'.

Still preferably, the proximal portion 4 is provided with a fifth fastening orifice 8E (second tibial fastening orifice), distinct from said fourth fastening orifice 8D, and which is configured so as to receive and guide a fifth fastening means 9E according to a fifth fastening direction $F_5$-$F_5$', in order to also fasten said nail 1 to said tibia Ti. Preferably, said fifth fastening direction $F_5$-$F_5$' is orthogonal to the first direction of extension A-A' of the proximal portion 2 of the nail 1. Advantageously, the main axis of extension of said fifth fastening orifice 8E through the nail 1 is coincident with said fifth fastening direction $F_5$-$F_5$'. Such a configuration with two tibial fastening orifices 8D, 8E is preferred because it guarantees a priori a better holding of the proximal portion 2 of the nail 1 within the tibia Ti.

As illustrated, said fourth 8D and fifth 8E fastening orifices are positioned one beneath the other according to the first direction of extension A-A' of the proximal portion 2 of the nail 1, centered with respect to said first direction of extension A-A'. Preferably, said fourth 8D and fifth 8E fastening orifices are positioned at the level of the portion the furthest from the proximal portion 2 of the nail 1 so as to improve even more anchorage of the nail in the tibia Ti.

Preferably, one amongst said fourth 8D and fifth 8E orifices has an oblong shape according to said first direction of extension A-A'. Where appropriate, the other one of the fourth 8D and fifth 8E fastening orifices may, in turn, be circular for example. In the example illustrated in the figures, the oblong-shaped fastening orifice is that one, amongst the fourth 8D and fifth 8E fastening orifices, is the furthest from the proximal end 3 of the nail 1.

Advantageously, such an oblong-shaped fastening orifice allows, in combination with the corresponding fastening means, fastening the proximal portion 2 of the nail 1 to the tibia Ti while keeping some translational freedom of said nail 1 within said tibia Ti (dynamic fastening), in particular for the purpose of an operation of compressing the joint of the ankle, conducted by the surgeon, and aiming at bringing the calcaneus Ca close to the tibia Ti. The preferred combination, illustrated in the figures, of a fourth 8D oblong fastening orifice with a fifth non-oblong fastening orifice 8E advantageously allows firstly fastening the proximal portion 2 of the nail 1 to the tibia Ti in a dynamic manner (by cooperation of said fourth fastening orifice 8D and fourth fastening means 9D), in particular for the purpose of a subsequent operation of compressing the joint, before completely locking said proximal portion 2 to the tibia Ti, by cooperation of said fifth fastening orifice 8E and fifth fastening means 9E. Advantageously, the large diameter (measured according to the first direction of extension A-A') of these fourth 8D and/or fifth 8E oblong fastening orifice is comprised between 5 and 15 mm±1 mm, preferably equal to about 13 mm±1 mm.

Advantageously, the arthrodesis device according to the invention comprises all or part of the above-mentioned second 9B, third 9C, fourth 9D and fifth 9E fastening means. In the example illustrated in particular in FIGS. 5 and 6, these fastening means 9B, 9C, 9D, 9E consist of second 9B, third 9C, fourth 9D and fifth 9E fastening screws, as commonly known and used in the field. Possibly, said fastening screws 9B, 9C, 9D, 9E may be cannulated in order to facilitate the set-up thereof, for example using a Kirschner wire. That being said, all or part of said second 9, third 9C, fourth 9D and fifth 9E fastening means may alternatively consist of a nail, a staple a wire or other.

Preferably, said first A-A' and second B-B' directions of extension are inscribed within the same main plane P, as illustrated in particular in FIG. 1. The proximal 2 and distal 4 portions of the nail 1 are then advantageously coplanar. Still preferably, said nail 1 is configured and dimensioned so that, when said nail 1 is implanted in the joint of the ankle of the patient, said main plane P is substantially parallel to the sagittal plane of the patient. In other words, the nail 1 is advantageously shaped, configured, dimensioned, so that the respective first A-A' and second B-B' directions of extension of the proximal 2 and distal 4 portions of the nail 1 could be directed parallel to the sagittal plane of the patient during the implantation of the nail 1, yet without calling into question the function of the above-mentioned fastening orifices 8A, 8B, 8C, 8D, 8E.

Thus, said nail 1 is advantageously designed so as to be able to be implanted with said distal portion 4 directed rearwards of the ankle according to a substantially anterior-posterior direction. Said proximal 3 and distal 5 ends then have a shift therebetween in the main plane P, the distal end 5 being shifted only in the posterior directions (and no laterally, in the middle or else in the middle-/lateral-posterior direction). Indeed, it has been observed that such an orientation is particularly advantageous for the stability of the nail 1 within the joint of the treated ankle, which in fine promotes a proper osteosynthesis of the bone bodies of said joint while participating to comfort of the patient.

In the preferred embodiment illustrated in the figures, the longitudinal grooves 6 which, as mentioned hereinbefore, advantageously form a means for blocking the rotation of the nail 1 about said first direction of extension A-A', are preferably arranged symmetrically on either side of said main plane P, in order to facilitate identification of the orientation of the plane P in the space by the surgeon.

Advantageously, the nail 1 is provided with a marker element 7 of the orientation of the main plane P in the space, in order to assist the surgeon in positioning the latter substantially parallel to the sagittal plane of the patient during the operation of implanting the nail 1 in the joint of the ankle. In the example illustrated in the figures, this marker element 7 preferably consists of a notch 7, which is formed in the nail 1 at the level of its free distal end 5 and which extends according to a main direction parallel to the main plane P (and preferably, inscribed within said main plane P). Preferably, said notch 7 opens onto only one amongst the front (i.e. intended to be directed forwards of the ankle) and rear (i.e. intended to be directed rearwards of the ankle) of the nail 1, for example of the front face (FIG. 5), so as to inform the surgeon not only about the orientation of the main plane P in the space, but also about the orientation of the distal plane 4 of the nail 1. Of course, said notch 7 may be replaced by any other suitable marker element means.

Even more preferably, said nail 1 is configured so that, when said nail 1 is implanted in the joint of the ankle of the patient, said main plane P is then coincident with a substantially vertical plane comprising the average main axis of the collar of the concerned calcaneus Ca. Such a configuration advantageously allows obtaining a proper middle-lateral centering of the distal portion 4 of the nail 1 in the bone mass of the calcaneus Ca.

Figure 4:
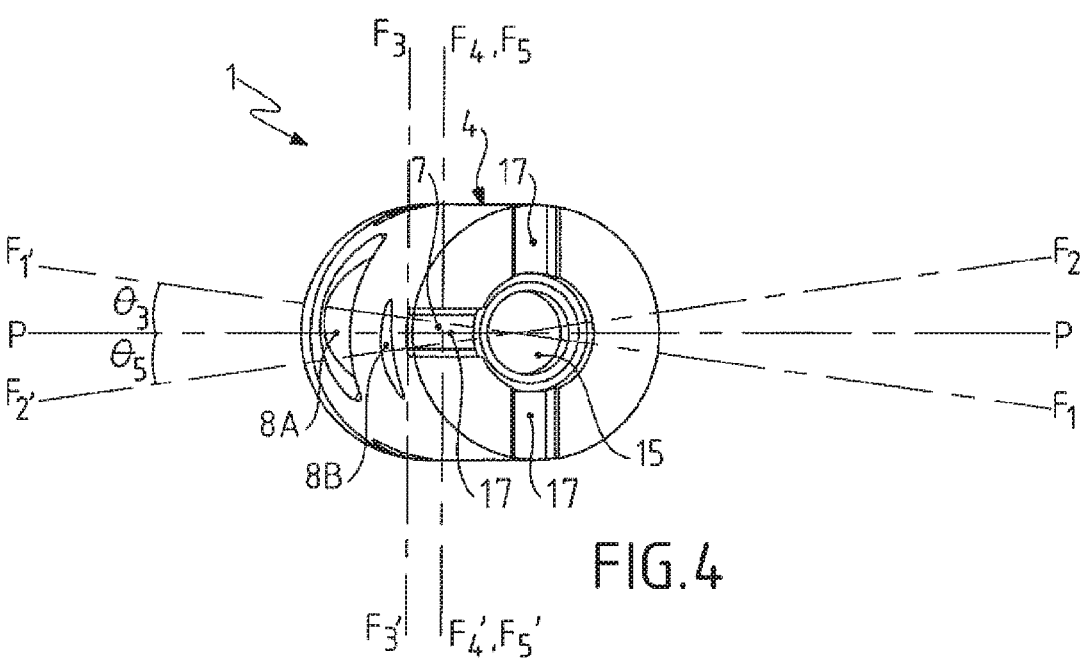
FIG. 4 illustrates, in a bottom view, the nail of FIGS. 1 to 3, the first direction of extension of the proximal portion of the nail being orthogonal to the plane of the figure.

Preferably, said first fastening direction $F_1$-$F_1'$ is:

on the one hand, secant to said first direction of extension A-A' of the proximal portion 2 of the nail 1 according to a second angle $\theta_2$ preferably equal to 45°±3° (FIG. 1), and on the other hand, secant to said main plane P according to a third angle $\theta_3$ preferably equal to 9°±2° (FIG. 4).

Figure 6:
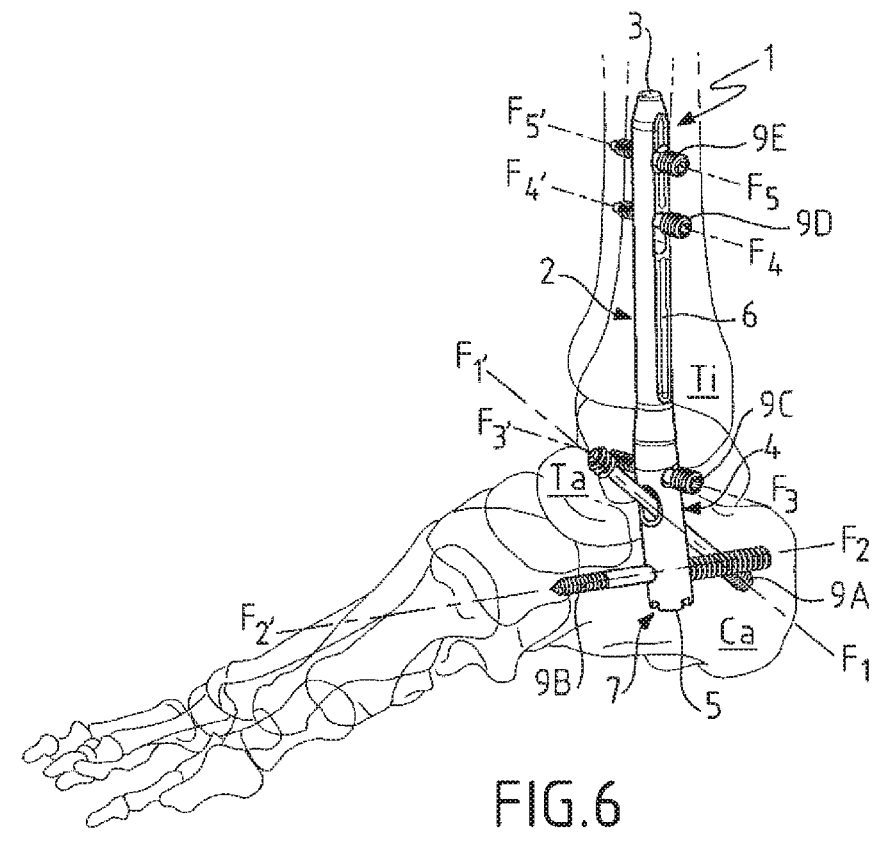

Thus, once the nail 1 is implanted, said first fastening means 9A may be set in place in the talus Ta and the calcaneus C of the patient via the first fastening orifice 8A, according to said first direction F1-F1' which is then directed in an oblique top-down manner from the front and from the inside of the ankle (anterior-middle) towards the rear and the outside of the latter (posterior-lateral). Given the respective morphologies of the calcaneus C and of the talus Ta, such an orientation of the first fastening direction F1-F1' allows advantageously optimizing the length of travel available for the first fastening means 9A within the respective bone mass of said calcaneus Ca and talus T, and therefore obtain an optimum anchorage of the nail 1 in the latter via said first fastening means 9A. Such a configuration of the first fastening orifice 8A advantageously enables the set-up of said first fastening means 9A by the front of the ankle, in particular by the upper front face of the talus Ta (FIGS. 5 and 6).

Preferably, said second fastening direction $F_2$-$F_2'$ is:

on the one hand, secant to said first direction A-A' of the proximal portion 2 of the nail 1 according to a fourth angle 84 equal to 78°±3°, and on the other hand, secant to said main plane P according to a fifth angle $\theta_5$ equal to 8°±2.

Thus, when the nail 1 is implanted, said second fastening means 8B may be set in place within the calcaneus Ca of the patient, according to said second direction $F_2$-$F_2'$ which is then directed in an oblique bottom-up manner from the rear and from the outside of the ankle (posterior-lateral) towards the front and the inside (anterior-middle) of the latter. Said second fastening direction $F_2$-$F_2'$ is then preferably inscribed within a vertical plane which is secant to the corresponding vertical plane within which the first fastening direction $F_1$-$F_1'$ is inscribed. Given the general morphology of the calcaneus Ca, such an orientation of the second fastening direction $F_2$-$F_2'$ advantageously allows optimizing the length of travel available for the second fastening means 8B within the bone mass of said calcaneus Ca, and therefore obtaining an optimum anchorage of the nail 1 in the latter via said second fastening means 9B.

Preferably, said third fastening direction $F_3$-$F_3'$ is orthogonal to said main plane P, within which are preferably inscribed the respective first A-A' and second B-B' directions of extension of the proximal 2 and distal 4 portions of the nail 1. Thus, when the nail 1 is implanted, said main plane P being substantially parallel to the sagittal plane of the patient, the third fastening direction $F_3$-$F_3'$ advantageously constitutes a middle-lateral talar fastening direction. The cooperation of this third fastening orifice 8C of the nail 1 with said third fastening means 9C advantageously participates in immobilizing the tibiotalar joint of the ankle.

Preferably, said fourth fastening direction $F_4$-$F_4'$ is orthogonal to said main plane P, within which are preferably inscribed the respective first A-A' and second B-B' directions of extension of the proximal 2 and distal 4 portions of the nail 1. Preferably, said fifth fastening direction $F_5$-$F_5'$ is parallel to said fourth fastening direction $F_4$-$F_4'$, which allows simplifying the set-up and fastening of the nail 1 by the surgeon.

In the preferred embodiment illustrated in the figures, the fourth 8D and fifth 8E fastening orifices are directed so that said corresponding fourth $F_4$-$F_4'$ and fifth $F_5$-$F_5'$ fastening directions are parallel to one another and orthogonal to said main plane P. Thus, when the nail 1 is implanted, said main plane P being substantially parallel to the sagittal plane of the patient, the fourth $F_4$-$F_4'$ and fifth $F_5$-$F_5'$ fastening directions advantageously constitute first and second tibial middle-lateral fastening directions respectively.

The osteosynthesis device according to the invention may possibly comprise a plurality of nails in accordance with the description provided hereinbefore, and thus advantageously constitute an osteosynthesis kit. These nails may have an identical respective distal portion and a respective proximal portion with a different length $L_2$ and/or diameter. Furthermore, said nails may be provided in a right version (as illustrated in the figures) and in a left version. Such a kit will enable the surgeon to best fit to the anatomy of the patient to be treated, and in particular to the anatomy of the calcaneus, talus and tibia of the latter.

Figures 7, 8, 9:
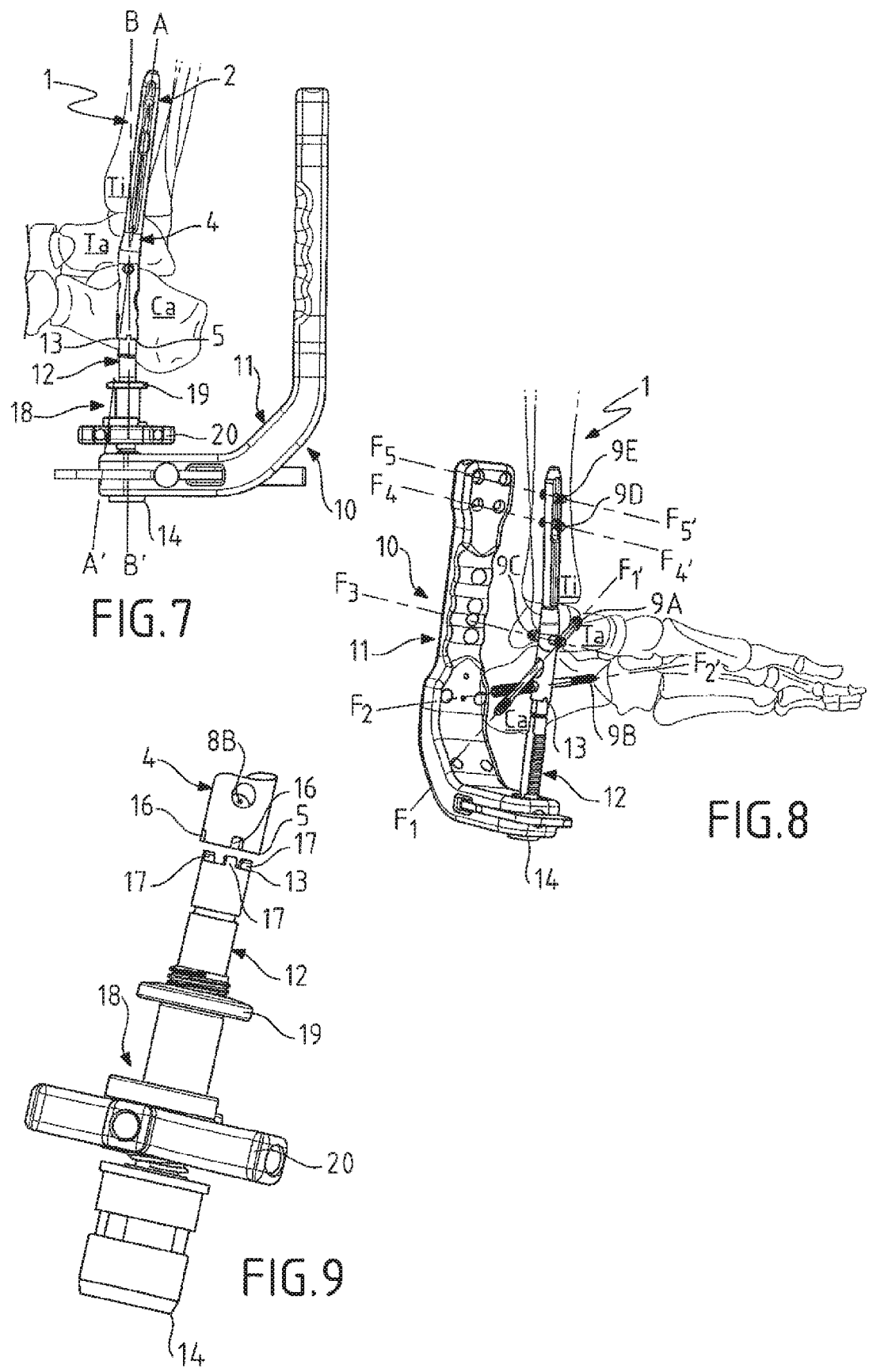
FIGS. 7 and 8 illustrate the nail of the previous figures, implanted in a joint of a right ankle of a patient, in connection with an outer instrument for setting said nail in place.
FIG. 9 illustrates, according to a perspective view, a detail of the instrument of FIG. 7 and of the distal portion of the nail of FIGS. 1 to 3.

Preferably, the osteosynthesis device according to the invention further comprises an instrument 10 for setting up said nail 1 within said joint of the ankle of the patient, preferably through a plantar approach. Such an instrument 10 is represented in FIGS. 7 and 8, in combination with the nail 1. Preferably, the instrument 10 comprises an arm 11, advantageously adapted to be manually gripped by the surgeon. Preferably, said instrument 10 is designed so as to be removably coupled to the distal end 5 of said nail 1. In this respect, the instrument 10 advantageously comprises a removable interface means 12 (or connector) to link the arm 10 to the nail 1. Preferably, said interface means 12 is, in turn, designed so as to be removable assembled to the arm 11, so that it is possible to firstly assemble the interface means 12 to the nail 1, then secondly assemble the interface means 12 to the arm 11.

As illustrated in particular in FIG. 8, said interface means 12 forms a substantially tubular part, which preferably extends longitudinally between a first 13 and a second 14 ends. Said interface means 12 preferably comprises an inner connecting screw (not illustrated) axially mounted within the interface means 12, and whose tapped distal portion projects out of the interface means 12 from the first end 13 of the latter, so as to form a tapped endpiece at the level of said first end 13. Advantageously, the head of the connecting screw is accessible via said second end 14.

Preferably, the nail 1 is, in turn, provided with a threaded hole 15 intended to cooperate with said connecting screw of the interface means 12 so as to couple the latter, and therefore the instrument 10, to the free distal end 5 of said nail 1. Said threaded hole 15, shown in particular in FIG. 4, advantageously extends through the distal portion 4 of the nail 1, from the free distal end 5 of the latter, and coaxially with the second direction of extension B-B' of said distal portion 4. As illustrated in FIGS. 7 and 8, the nail 1 thus advantageously rests on the interface means 12, the second direction of extension B-B' of the distal portion 4 of the nail 1 being aligned with the corresponding axis of longitudinal extension of the interface means 12, such that a displacement of the interface means 12 causes a substantially identical displacement of the nail 1.

In order to facilitate the positioning and coupling of the nail 1 with respect to the interface means 12 and limit the risk of the surgeon being mistaken in the orientation of the nail 1, the interface means 12 and the nail 1 advantageously include complementary marker means 16, 17. As represented in FIGS. 4 and 9, the marker means 16, 17 are preferably formed by three lugs 16 and three notches 17 arranged such that each notch 17 could cooperate with only one corresponding lug 16.

Preferably, the notches 17 are formed in the free distal end 5 of the nail 1 intended to come into contact with the corresponding first end 13 of the interface means 12 in which are formed the lugs 16. Of course, a reverse configuration, in which the nail 1 would be provided with lugs intended to cooperate with corresponding notches formed on the interface means 12, could also be considered. Preferably, the marker means 16, 17 therefore comprise three pairs each formed by complementary lug 16 and notch 17, said pairs being located on the circumference of the junction between the nail 1 and the interface means 12, and oriented substantially 90° with respect to one another. Such a configuration of the marker means 16, 17 allows in particular avoiding the surgeon assembling the nail 1 with respect to the instrument 10 in an orientation other than the intended one, and in particular according to an orientation such that, once the nail 1 is implanted, the distal portion 4 of the latter would not be directed rearwards of the ankle of the patient.

Preferably, one of said notches 17 is coincident with the aforementioned notch 7 (FIG. 4), which advantageously forms a marker element 7 of the orientation of the main plane P of the nail 1. Advantageously, the other notches 17 are then aligned according to a direction orthogonal to the main plane P (FIG. 4). Thus, said marker means 16, 17 advantageously participate to guiding the surgeon during the implantation of the nail 1 in the joint of the ankle of the patient, in particular so that the latter could position the nail 1 so that said main plane P of the latter is parallel to the sagittal plane of the patient.

As represented in FIGS. 7 and 8, the nail 1 may thus advantageously be linked to the interface means 12 by the first end 13 of the latter, so as to occupy a stable and fixed position of insertion of the nail 1 into the body of the patient.

As illustrated in FIGS. 7 and 9, said instrument 10 advantageously comprises a means 18 for compressing (omitted in FIG. 8) the joint of the ankle, intended to allow bringing the calcaneus Ca and the tibia Ti forming said joint close to one another. Preferably, said compression system 18 comprises a bearing surface 19 designed so as to bear against the sole of the foot of the patient, opposite the calcaneus Ca, and prone to be displaced so as to exert a pressure against the latter, so as to thereby bring the calcaneus Ca close to the tibia Ti, and preferably bringing the calcaneus Ca and the talus Ta close to the tibia Ti.

Preferably, said bearing surface 19 is mounted according to a slide connection relative to the interface means 12 so as to evolve, preferably according to a direction collinear with the axis of longitudinal extension of the interface means 12, between at least one inactive position (FIG. 7), in which the bearing surface 19 is not in contact with the sole of the foot of the patient, and at least one active position (not illustrated), in which said bearing surface comes into bearing contact against the sole of the foot of the patient, opposite the calcaneus, and compresses the joint, thereby brining the calcaneus Ca close to the tibia Ti.

Preferably, said compression means 18 further comprises a control means 20, such as a for example a knob 20 or a scroll wheel, designed and arranged so as to generate, via said interface means 12, a displacement of the bearing surface 19 between said inactive and active positions. Advantageously, said control means 20 is mounted with respect to the interface means 12 according to a helical connection having a direction coincident with the axis of longitudinal extension of the interface means 12, so that the rotation of the control means 20 about the axis of extension of the interface means 12 causes a translation of the bearing surface according to the same axis.

Preferably, said instrument 10 constitutes a drill and/or aim guide for the set-up of all or part of the first 9A, second 9B, third 9C, fourth 9D and fifth $9^E$ fastening means of the nail 1. In this respect, as shown in FIG. 9, the arm 11 of the instrument 10 may be provided with a determined number of drill and/or aim orifices, each being configured so as to form through said arm 11 a conduit whose main axis of extension is collinear with at least one amongst the first $F_1$-$F_1'$, second $F_2$-$F_2'$, third $F_3$-$F_3'$, fourth $F_4$-$F_4'$ and fifth $F_5$-$F_5'$ fastening directions of the first 8A, second 8B, third 8C, fourth 8D and fifth 8E fastening orifices, when the instrument 10 is coupled to the nail 1.

The invention also concerns a surgical method for carrying out an arthrodesis of an ankle joint, in which an arthrodesis device is used, comprising a nail 1 intended to be implanted in a tibia Ti, a talus Ta and a calcaneus Ca of a patient, said nail 1 comprising:

a proximal portion 2 which generally extends according to a first longitudinal direction of extension A-A', and a distal end 4 which prolongs said proximal portion 2 and generally extends according to a second longitudinal direction of extension B-B', said first A-A' and second B-B' directions of extension being secant, said distal portion 4 being provided with a first fastening orifice 8A.

Advantageously, said surgical method implements an arthrodesis device in accordance with that according to the invention, so that the description that has been made hereinbefore of the latter remains applicable mutatis mutandis to the present surgical method. Thus, the nail 1 implemented in the context of said surgical method is designed and configured so that, when said nail 1 is implanted with said distal portion 4 directed rearwards of the ankle of the patient, said first fastening orifice 8A is arranged, directed, so as to receive and guide a first fastening means 9A according to a first fastening direction F1-F1' which extends through said talus Ta and calcaneus a in order to fasten said nail 1 to said talus Ta and to said calcaneus Ca.

Said surgical method comprises at least one first step during which said nail 1 is set in place within the joint of the ankle of the patient. Advantageously, this first set-up step may be preceded by a preparatory step during which a room is made, using any known means (for example, using a cannulated drill bit), within said tibia Ti, talus Ta and calcaneus Ca, in order to subsequently receive said nail 1, during said first step of setting the latter in place. Preferably, this room is made so as to enable the set-up of said nail 1 through a backward plantar approach. This preparatory step may possibly be preceded or followed by a step of properly preparing the joint of the ankle to be treated, involving for example bone sections and an extraction of cartilaginous elements between the tibia Ti and the talus Ta (tibiotalar joint) on the one hand and between the talus Ta and the calcaneus Ca (talocalcaneal joint) on the other hand, so as to suppress all or part of the natural joint surfaces of the joint of the ankle to be treated.

During said first step of setting the nail 1 in place, the latter is implanted in the joint of the ankle so that said distal portion 4 of the nail 1 is directed rearwards of the ankle of the patient.

Preferably, the respective first A-A' and second B-B' directions of extension of the proximal 2 and distal 4 portions of the nail 1 implemented by said surgical method are inscribed within the same main plane P. Preferably, the nail 1 is then implanted, during said first step, so that said distal portion 4 of the nail 1 is directed rearwards of the ankle of the patient and that said main plane P is substantially parallel to the sagittal plane of the patient. Even more preferably, the nail 1 is then implanted, during said first step, so that said distal portion 4 of the nail 1 is directed rearwards of the ankle of the patient and that said main plane P is coincident with a substantially vertical plane comprising the average main axis of the collar of the calcaneus Ca. Control of such an orientation may advantageously be facilitated by the implementation of the instrument 10 described hereinbefore, in particular by cooperation of the complementary marker means 16, 17 that the interface means 12 of the instrument 10 and the nail 1 preferably include, and/or by a radiographic monitoring.

Preferably, the first step of setting said nail 1 in place is followed by a second step during which the nail 1 is fastened to the tibia Ti, via a fourth 8D and/or a fifth 8E fastening orifice(s), and using a fourth 9D and/or fifth 9E fastening means received and guided within said corresponding fourth 8D and/or fifth 8E fastening orifice(s). Preferably, said fourth 9D and fifth 9E fastening means are set in place through a middle-lateral approach.

Preferably, said second step of fastening the nail 1 to the tibia Ti is followed by a third step during which the joint of the ankle is compressed, in order to bring the calcaneus close to the tibia Ti, and preferably in order to bring the calcaneus Ca and the talus Ta close to the tibia Ti. For example, this third step may be carried out manually, through a pressure on the foot, or using a means 20 for compressing the instrument 10 previously described in connection with the arthrodesis device according to the invention.

Preferably, said third step of compressing the joint of the ankle is followed by a fourth step during which the nail 1 is fastened to the talus Ta, via a third fastening orifice 8C, and using a third fastening means 9C received and guided within said third fastening orifice 8C. Preferably, said third fastening means 9C is set in place through a middle-lateral approach. Thus, said fourth step advantageously aims at fastening the nail 1 by immobilizing the tibiotalar joint. Preferably, said third fastening means 9C then crosses (or at least partially crosses) only the talus Ta.

Preferably, said fourth step of fastening the nail 1 to the talus Ta is followed by a fifth step during which the nail 1 is simultaneously fastened to the talus Ta and to the calcaneus Ca via said fastening orifice 8A, and using said first fastening means 9A received and guided within said first fastening orifice 8A. Thus, said fifth step advantageously aims at fastening the nail 1 by immobilizing the talocalcaneal joint. Advantageously, it constitutes a step of transarticular fastening of the nail 1. Advantageously, the first fastening means 9A used during said fifth step consists of a compressive screw 9A. Said fourth fastening step then advantageously comprises an operation of compressing the talocalcaneal joint by tightening said compressive screw 9A into the talus Ta and the calcaneus Ca. Preferably, the first fastening means 9A is set in place by the front of the ankle, so that it successively crosses (at least partially) the talus Ta, the nail 1 and the calcaneus Ca.

Preferably, said fifth step of simultaneously fastening the nail to the talus Ta and to the calcaneus Ca is followed by a sixth step during which the nail 1 is fastened to the calcaneus Ca via said second fastening orifice 8B, and using said second fastening means 9B received and guided within said second fastening orifice 8B. Preferably, said second fastening means 9B then crosses (or at least partially crosses) only the calcaneus Ca. Preferably, the second fastening means 9B is set in place by the rear of the ankle.

Of course, the different steps described hereinabove may be carried out in an order different from that which has just been exposed. Moreover, some of these steps may possibly be omitted or modified. For example, said first step may be followed by said fifth step, followed by said fourth step, followed by said second step, and finally followed by said third step.

Advantageously, all or part of the above-described steps may be implemented using the previously-described instrument 10 in connection with the arthrodesis device according to the invention.

For all practical purposes, it should be noted that the term «first», «second», «third», etc. used in the present description preferably have no ordinal or cardinal connotation, that is to say they do not involve herein any notion pertaining to the order, the amount or any other classification of the elements or components to which these terms are related. In this instance, they are intended only to facilitate the understanding of the invention by allowing differentiating some technical features that the arthrodesis device according to the invention might have, as well as the different steps that the surgical method for advantageous implementation of said arthrodesis device might advantageously comprise.

Also, the terms «posterior», «anterior», «middle» and «lateral» are preferably used in the present description to describe elements or features in connection with their respective orientation with respect to the body of the patient, in normal use of the arthrodesis device according to the invention, and in particular of the nail 1 of the latter. Thus, the term «middle» is preferably used to refer to an element or component of the arthrodesis device that is intended to be positioned or oriented on the side the closest to the midsagittal axis (or middle axis) of the body of the patient, in other words on the side oriented inwardly of the ankle and of the leg of the patient. In contrast, the term «lateral» is used in connection with the side the furthest from the midsagittal axis. According to the same logics, the terms «posterior» and «anterior» preferably refer respectively to a rearward, respectively forward, positioning with respect to the frontal plane of the patient.

POSSIBILITY OF INDUSTRIAL APPLICATION

The invention finds its industrial application in the design and manufacture of devices intended to be used to carry out an arthrodesis and, more specifically, in the design and manufacture of devices intended to be used to carry out an arthrodesis of the joint of an ankle, in particular in the context of an orthopedic treatment.

The invention claimed is:

1. An ankle arthrodesis device comprising a nail configured for implantation in a tibia, a talus and a calcaneus of a patient, the nail comprising:

a proximal portion which generally extends according to a first longitudinal direction of extension;

a distal portion which extends from the proximal portion and generally extends according to a second longitudinal direction of extension with respect to the first longitudinal direction of extension, the distal portion being provided with a first fastening orifice which is oblong according to the second longitudinal direction of extension;

wherein the distal portion of the nail is adapted to extend through the calcaneus in an oblique configuration with respect to an axis of vertical extension of the tibia;

the device comprising a first compressive fastening means, comprising a compressive screw, the nail being designed and configured so that, when the nail is implanted with said distal portion directed rearwards of the ankle of the patient, said first fastening orifice is arranged so as to receive and guide the first fastening means according to a first fastening direction which is adapted to extend through the talus and calcaneus so as to fasten the nail to the talus and the said calcaneus;

wherein an oblong-shaped fastening orifice is configured to fasten the proximal portion of the nail to the tibia while keeping translational freedom of the nail within the tibia;

wherein a third second fastening direction $F_3$-$F_3'$ is orthogonal with respect to a main plane, comprising one or more directions of extensions of the proximal and distal portions of the nail;

the third second fastening direction $F_3$-$F_3'$ comprising a middle-lateral talar fastening direction;

a longitudinal groove configured to block rotation of the nail about the first longitudinal direction of the extension, the longitudinal groove arranged symmetrically on either side of a main plane, thereby facilitating identification of an orientation of the main plane;

wherein the extensions are inscribed within the main plane;

a marker element comprising a notch formed in the nail at a level of a free distal end; and an instrument comprising a removable and tubular interface that sets the nail in place using a plantar approach, the instrument configured to be removably coupled to a distal end of the nail.

2. The device according to claim 1, wherein the first and second directions of extension comprise a first angle comprised between 5 and 10°.

3. The device according to claim 1, wherein the nail is configured and dimensioned so that, when the nail is implanted, the main plane is configured to be parallel to a sagittal plane of the patient.

4. The device according to claim 1, wherein the distal portion is provided with a second fastening orifice, which is configured to receive and guide a second fastening means according to a second fastening direction, thereby configured to fasten the nail to the calcaneus.

5. The device according to claim 1, wherein the proximal portion further comprises an additional fastening orifice, which is configured to receive and guide an additional fastening means according to an additional fastening direction.

6. The device according to claim 5, wherein the additional fastening direction is orthogonal to the main plane.

7. The device according to claim 6, wherein the additional fastening orifices has an oblong shape according to the first direction of extension.

8. A method for carrying out an arthrodesis of an ankle joint of a patient, comprising:

setting a nail in place within the joint of the ankle patient, wherein during a step of setting the nail in place, the nail is:

implanted in the joint of the ankle so that a distal portion of the nail is directed rearwards of the ankle of the patient and simultaneously fastened to a talus and to a calcaneus via a fastening orifice, using a first compressive fastening means received and guided within the first fastening orifice;

wherein an oblong-shaped fastening orifice is configured to fasten a proximal portion of the nail to the tibia while keeping translational freedom of the nail within the tibia;

wherein a longitudinal groove is configured to block rotation of the nail about a first longitudinal direction of extension, the longitudinal groove arranged symmetrically on either side of a main plane;

configuring a third fastening direction $F_3$-$F_3'$ in an orthogonal orientation with respect to the main plane, comprising one or more directions of extension of the proximal and distal portions of the nail;

adapting the distal portion of the nail to extend through the calcaneus in an oblique configuration with respect to an axis of vertical extension of the tibia;

wherein the directions of extension are inscribed within the main plane;

the third fastening direction $F_3$-$F_3'$ comprising a middle-lateral talar fastening direction;

a marker element comprising a notch formed in the nail at a level of a free distal end; and providing an instrument comprising a removable and tubular interface that sets the nail in place within the joint of the ankle of the patient through a plantar approach, wherein the instrument may be removably coupled to a distal end of the nail.

* * * * *